US005714672A

United States Patent [19]

Fehr et al.

[11] Patent Number: 5,714,672
[45] Date of Patent: Feb. 3, 1998

[54] SOYBEAN DESIGNATED ELGINEMS-421

[75] Inventors: Walter R. Fehr; Earl G. Hammond, both of Ames, Iowa

[73] Assignee: Iowa State University Research Foundation, Inc., Ames, Iowa

[21] Appl. No.: 686,529

[22] Filed: Jul. 26, 1996

Related U.S. Application Data

[62] Division of Ser. No. 376,466, Jan. 20, 1995, Pat. No. 5,602,311, which is a continuation of Ser. No. 180,114, Jan. 12, 1994, abandoned, which is a continuation of Ser. No. 839,328, Feb. 20, 1992, abandoned, which is a continuation-in-part of Ser. No. 461,341, Jan. 5, 1990, abandoned.

[51] Int. Cl.$^6$ ................ A01H 5/00; A01H 5/10; C12N 15/01

[52] U.S. Cl. ............. 800/200; 800/230; 800/250; 800/DIG. 26; 800/DIG. 69; 435/172.1; 426/601

[58] Field of Search ................ 800/200, 230, 800/250, DIG. 26, DIG. 69; 435/172.1; 426/601

[56] References Cited

PUBLICATIONS

Fehr et al., Crop Sci. 24:385–386, Registration of 'Elgin' soybean 1984.

"Notice to Plant Breeders and Seed Producers Relative to Release of Soybean Germplasm N85–2124, N85–2131, and N85–2176", Dr. R.J. Kuhr et al. (1987).

"Notice of Release of Soybean Germplasm with Altered Levels of Palmitic Acid", M.E. Carter et al., (1988).

"Chapter 21 Processing and Utilization", T.L. Mounts et al., *Soybeans: Improvement, Production, and Uses—Agronomy Monograph*, No. 16, (1987), pp. 819–845, 860–865.

"Old and New in Winterizing", George M. Neumunz, *J. Am. Oil Chemists' Society*, (1978), vol. 55:396A–398A.

"Fatty Acid Composition of Margarines, Processed Fats, and Oils: A New Compilation of Data for Tables of Food Composition", John L. Weihrauch et al., *Food Technology*, Feb. 1977, vol. 31, pp. 80–85 and 91.

"Fatty Acid Development in a Soybean Mutant with High Stearic Acid", G.L. Graef et al., *Journal of American Oil Chemists' Society*, vol. 62, No. 4, Apr. 1985, pp. 773–775.

"Genetic Alteration of Soybean Oil Composition by a Chemical Mutagen", J.R. Wilcox et al., *Journal of American Oil Chemists Society*, vol. 61, No. 1, (Jan. 1984), pp. 97–100.

"Progress in the Selection For Altered Fatty Acid Composition in Soybeans", Richard F. Wilson et al., *Crop Science*, vol. 21, Sep.–Oct. 1981, pp. 788–791.

"Recurrent Selection in Soybeans. IV. Selection for Increased Oleic Acid Percentage in Seed Oil", J.W. Burton et al. *Crop Science*, vol. 23, Jul.–Aug. 1983, pp. 744–747.

"Fatty Acid Composition of the Oil in Reciprocal Crosses Among Soybean Mutants", E.A. Erickson et al., *Crop Science*, vol. 28, Jul.–Aug. 1988, pp. 644–646.

"Inheritance of Palmitic and Stearic Acid Mutants of Soybean", D.M. Bubeck et al., *Crop Science*, vol. 29, May–Jun. 1989, pp. 652–656.

"Soybean Protein and Oil Quality", J.R. Wilcox, *IV Conferencia Mundial de* Investigacion en *Soja (World Soybean Research Conference IV)* Mar. 5–9, 1989, Buenos Aires, Argentina, pp. 28–39.

*Primary Examiner*—Elizabeth F. McElwain
*Attorney, Agent, or Firm*—Burns, Doane, Swecker & Mathis, L.L.P.

[57] ABSTRACT

A novel soybean seed and plant designated ElginEMS-421 having ATCC Accession No. 97617 and its descendents are provided. Such soybean seed exhibits an elevated palmitic acid (C16:0) content of at least 15.7% by weight based upon the total fatty acid content in the endogenously formed vegetable oil.

4 Claims, No Drawings

SOYBEAN DESIGNATED ELGINEMS-421

This Application is a division of Ser. No. 08/376,466, filed Jan. 20, 1995 (now U.S. Pat. No. 5,602,311), which is a continuation of Ser. No. 08/180,114, filed Jan. 12, 1994 (now abandoned), which is a continuation of Ser. No. 07/839,328, filed Feb. 20, 1992 (now abandoned), which is a continuation-in-part of Ser. No. 07/461,341, filed Jan. 5, 1990 (now abandoned).

FIELD OF THE INVENTION

This invention relates to novel soybean seeds and products of soybean seeds, such as soybean oil, and, more particularly, to soybeans seeds and products characterized by extremely high levels of palmitic acid.

BACKGROUND OF THE INVENTION

Soybean seeds represent perhaps the most significant oilseed in the world. Soybean oil makes up approximately 28% of the world supply of fats and oils, has been considered to be the major vegetable oil produced and consumed in the United States, and more than 90% of the soybean oil is used in food products (World Soybean Research Conference III Proceeding, Shibles, R. (Ed.) 1985).

Soybeans thus represent a significant world-wide food source, providing an excellent source of protein. As such, soybeans represent potential alternatives to meats.

Tofu and soymilk are two principal food products derived from soybean seeds. More than one billion people in China and Southeast Asia, it has been stated, rely on tofu as a major food protein source. (Proc. Int. Soya Protein Food Conf., American Soybean Assoc., p. 35 (1970)). Soymilk is similarly an important source for food protein.

One application for which soybean oil may be used is the production of plastic fats (e.g.—shortenings and margarines). Such plastic fats are made with a matrix of solid fats whose interstices are filled with liquid oil. Solid fats can crystallize in several forms with different melting points and physical properties. The forms are commonly designated alpha, beta' and beta, with the beta form having the highest melting point and the greatest stability. Forms other than these three may also be present. The beta' form generally has the properties that are most usually desired in a plastic fat.

If the solid portion of the plastic fat contains about 15% or more of palmitic acid and the rest is stearic acid, it will stabilize in the beta' form. If the ratio of stearic/palmitic is higher, then the fat may convert to the beta form with its less desirable physical structure.

Soybean oil will most usually contain a level of about 10% palmitic acid or so. Accordingly, if such soybean oil is hydrogenated and made into a plastic fat, it will likely crystallize in the beta form. To prevent this, an oil such as cottonseed or palm oil that is richer in palmitic acid is blended with the soybean oil.

The use of either palm oil or cottonseed oil presents some difficulties. Some users thus consider palm oil to be undesirable based upon perceived health considerations. On the other hand, cottonseed oil is generally available only in limited amounts at a higher price than that of soybean oil. It would accordingly be highly desirable to be able to provide soybean varieties having sufficiently elevated palmitic acid contents so that plastic fats can be produced such that such products will stabilize in the beta' form.

Further, some producers for some plastic fat applications believe that soybean oil having a palmitic acid content in the range of about 13% or 14% to about 16% or so is preferred. For such applications, it would be highly desirable to be able to provide soybean varieties having a sufficiently high level of palmitic acid to use for blending with soybean varieties having more conventional palmitic acid contents to provide the desired intermediate range of palmitic acid content.

The palmitic acid levels in soybean seed oil range from 9.3% to 17.4% within the world collection (Erickson et al., *Journal of Heredity*, 79, p. 465, 1988). The Erickson et al. article reports the inheritance of altered palmitic acid percentages in two soybean mutants, C1726 and C1727. The level of palmitic acid in C1727 reported averages 17.3% palmitic acid in comparison to 11.5% in the oil of the parent cultivar "Century."

Despite the clear need for soybeans having a level of palmitic acid above that present in the world collection at the present time, this objective still remains to be achieved.

SUMMARY OF THE INVENTION

It has been discovered that a mutant line obtained from the parent variety Asgrow A1937 provides a population of soybean seeds exhibiting high levels of palmitic acid. The palmitic acid concentration capable of being obtained is about 18% of the total fatty acid present, even up to 20% or more.

Further, it has been discovered that crossing the Asgrow A1937 mutant with a second mutant provides a population of soybean seeds exhibiting significantly higher levels of palmitic acid than have been capable of being achieved. More particularly, soybean seeds having palmitic acid contents above about 20%, and, more preferably, of at least about 25% or more, have been achieved. Still further, it has been discovered that soybean seeds having palmitic acid contents of 30.0% or more may be obtained by crossing selected progeny with line A89-259098.

If desired, the soybeans of the present invention can be used as a donor parent in a backcrossing program with any desired commercial cultivar as a recurrent parent to isolate a commercial variety having desirable seed yield and other agronomic characteristics in addition to the high level of palmitic acid.

DETAILED DESCRIPTION OF PREFERRED EMBODIMENT

According to one aspect of the present invention, the novel soybean seeds and plants characterized by palmitic acid contents of at least 18% were obtained by preparation of a mutant line developed by treating the cultivar Asgrow A1937 with nitroso methyl urea (NMU). The mutation procedure utilized will be described in detail hereinafter in the Examples. The mutant line has been designated A1937NMU-85.

Pursuant to a further aspect of the present invention, crossing of the parent mutant line A1937NMU-85 with a second mutant line, ElginEMS-421, has been found to provide a population of soybean seeds with palmitic acid contents significantly above that of the parent line Asgrow A1937. The preparation of the mutant line, ElginEMS-421, will be described in conjunction with the Examples.

Crossing of the parent mutant lines A1937NMU-85 and ElginEMS-421 to obtain the soybean lines of the present invention can be carried out by any desired hybrid formation technique. Standard hybridization techniques are, of course, well known and may be utilized. As an illustrative example, hybridization techniques are disclosed in Fehr, *Principles of*

*Cultivar Development*, Vol. 1, Theory and Technique, Chapter 13, pp. 156–164, Macmillan Publishing Company, New York, 1987, which hybridization techniques are herein incorporated by reference.

Progeny from the crossing of A1937NMU-85 and ElginEMS-421 yielded soybean seeds wherein the palmitic acid content is greater than 18%, preferably greater than about 20%, and more preferably, greater than about 25%.

The fatty acid composition was determined by gas-liquid chromatography using the method as generally outlined in Graef et al. (*Crop Sci.*, 25:1076–1079, 1985). Thus, in general, the method comprises (1) crushing the seed sample, (2) putting the crushed sample into a test tube with a hexane solvent and extracting the oil into the hexane, (3) the fatty acids in the oil are converted to their methyl esters using sodium methoxide and methanol, (4) water is added to inactivate the sodium methoxide catalyst, and (5) the methyl esters, which float to the top of the water layer, are diluted with hexane and become the sample that is introduced into the column of the gas chromatography apparatus.

As may be appreciated, this general methodology may be employed and specific aspects changed to lessen the time needed as desired. For example, the stationary phase selected for the columns will dictate the temperature at which the sample can be introduced.

None of the specifics utilized, e.g.—capillary versus packed columns, are considered to affect to any appreciable extent the results obtained for an analysis. Rather, such specifics affect the time required for sample preparation and analysis.

The percentages of the fatty acids set forth herein, unless otherwise designated, thus are on a weight basis and refer to the percentage of the methyl ester of palmitic acid or other fatty acid compared to the total methyl esters of the fatty acid composition in the sample being analyzed. This can also be taken as the weight percentage of the fatty acid itself because the difference between the palmitic acid content and that of its methyl ester as determined in the gas chromatography technique described herein is so minimal as may be ignored, as is commonly done in this field.

The gas chromatography techniques described herein are routinely used for analysis of the fatty acid composition of soybeans. The experimental error is considered to be within the range of from about 1 to 5% or so, depending upon the magnitude of the peak. For example, with a relatively large peak indicative of an oleic acid content of 50% or so, the experimental error may be as low as about 1% of the value, viz.—50±0.5%. At the other extreme, a small peak indicative of a stearic acid content of 4.0% may have an experimental error of about 5.0% of the value, viz.—4.0%±0.2. A palmitic acid content of about 20% lies in the middle, with the expected error being about 2–3% of the reported value, viz.—20%±0.4 or 0.6%.

As may be appreciated, the palmitic acid levels of the soybeans of the present invention set forth herein were obtained from soybeans grown in Iowa and Puerto Rico. Growth under climatic conditions cooler or warmer may result in a somewhat altered fatty acid composition. However, while the specific results may vary somewhat depending upon the specific growing conditions experienced, the progeny of the present invention will be characterized by extremely high palmitic acid contents relative to other soybean lines grown under similar conditions.

Progeny exhibiting the desired high palmitic acid trait can be crossed with other progeny to provide a population of soybean seeds having extremely high palmitic acid contents.

It can be expected that crosses utilizing the more desirable progeny should be capable of providing lines having palmitic acid contents up to about 30.0% or so.

Indeed, soybean lines having palmitic acid contents of 30.0% or more have been obtained by crossing selected progeny with line A89-259098. Parent line A89-259098 is described in our copending application, Ser. No. 07/643,277, the disclosure of said line being herein incorporated by reference. It can thus be expected that crosses utilizing the more desirable progeny should be capable of providing lines having palmitic acid contents up to about 35.0% or so.

Further, progeny can be crossed, if desired, with other progeny, or with any other soybean line or cultivar to yield a soybean cultivar having the desired seed yield or other desired agronomic traits as well as the desired high palmitic acid trait. Self-pollination of selected progeny may likewise yield lines having characteristics desired for some applications.

Any hybridization technique may be used, and many are known as has been described herein. For example, the selection of progeny having the desired high palmitic acid trait can be obtained by conducting backcrossing with a commercial variety until a desirable commercial variety has been isolated. Backcrossing techniques are known, as disclosed in Fehr, *Principles of Cultivar Development*, Vol. 1, Theory and Technique, Chapter 28, pp. 360–376, the disclosure of which is herein incorporated by reference.

As one example, backcrossing using the desired $F_2$ seeds obtained by natural self-pollination of the $F_1$ plants could be carried out as follows:

(1) Plant F, seeds obtained by crossing a parent with the desired high palmitic acid trait to the desired commercial cultivar (recurrent parent). Sample $F_2$ seeds from $F_1$ plants are analyzed for fatty acid concentration, and seeds with the desired high palmitic acid content are planted for backcrossing.

(2) Cross-pollinate the desired commercial cultivar (recurrent parent) with an $F_2$ plant having the high palmitic acid content.

(3) Plant the $BC_1F_1$ seeds and obtain $BC_1F_2$ seeds by natural self-pollination. Sample $BC_1F_2$ seeds are analyzed for fatty acid concentration, and those displaying the high palmitic acid trait are backcrossed to the recurrent parent.

(4) The backcross and selection procedure herein described (Step 3) can be repeated until lines with the desired high palmitic acid composition and agronomic performance are recovered. It is believed that four of these backcross cycles should serve to transfer the high palmitic acid trait to the desired cultivar (viz.—recurrent parent), although the number of such cycles can be fewer, or more, as is desired. The result is the production of a soybean line quite similar to the commercial cultivar except having the desired high palmitic acid content.

Any commercial cultivar (recurrent parent) desired may be employed for backcrossing. Factors such as, for example, seed yield, geographical area, and many others, as is known, will generally dictate the cultivar selected from the several hundred commercial cultivars available.

The following Examples are illustrative, but not in limitation, of the present invention. The gas chromatography results obtained from the instrument itself are reported to two decimal points (i.e.—"0.00"). As reported herein, the fatty acid values are set forth to one decimal point. Values of 6 or more in the second decimal point were raised (e.g.—

4.29 is reported herein as 4.3), values of 4 or less are ignored (e.g.—4.24 is reported as 4.2), values of 5 are raised if the first decimal is odd (e.g.—4.15 is reported as 4.2) and ignored if even (e.g.—4.25 is reported as

EXAMPLE 1

This Example describes the preparation of the mutant line A1937NMU-85.

Mutant line A1937NMU-85 was obtained from nitroso methyl urea (NMU) treatment of the parent variety Asgrow A1937. In May, 1985, 2,500 seeds of A1937 were soaked in 2.5 L distilled water in a 6 L flask for 9 hours at room temperature. The flask was aerated for the 9 hours of soaking. The water was drained from the flask, and 2.5 L of 2.5 mM NMU in 0.1 molar ["M"] phosphate buffer at pH 5.5 were added. The seeds were soaked with aeration for 3 hours, the solution was drained and the seeds were rinsed twice with distilled water. Treated seeds were placed in containers to prevent drying and transported to the Agricultural Engineering and Agronomy Research Center near Ames, Iowa. The seeds were planted 2.5 cm deep in moist soil within 4 hours after the last rinse. The soil was watered regularly to keep it moist until seeding emergence. The properties of the mutant seed and their progeny were evaluated beginning with the $M_4$ generation.

A similar number of seeds was harvested from each of the $M_1$ (first mutant generation) plants in the population to obtain 2,000 $M_2$ seeds. A random sample of 1,000 of the second generation $M_2$ seeds from the population was planted in October at the Iowa State University-University of Puerto Rico soybean nursery at Isabela, Puerto Rico. About 2,000 $M_3$ seeds were obtained by harvesting a similar number of seeds from each $M_2$ plant. In February, 1,000 $M_3$ seeds were planted in Puerto Rico. About 2,000 $M_4$ seeds were obtained by harvesting a similar number of seeds from each $M_3$ plant. In May, 1,000 $M_4$ seeds were planted at Ames. Five hundred Me plants were harvested individually from the population, and a 10-seed sample from selected plants was analyzed by gas-liquid chromatography to determine the fatty acid composition. $M_5$ progeny of selected plants were planted in Puerto Rico in February, 1987; and the results confirmed the unique fatty acid composition of the $M_4$ parent plant.

A 10-seed sample of the $M_4$ plant from which A1937NMU-85 originated and its parent was analyzed by gas-liquid chromatography, and the results are set forth in Table I:

TABLE I

| | Fatty Acid Composition | | | | |
|---|---|---|---|---|---|
| Seed Identification | Palmitic Acid (16:0) | Stearic Acid (18:0) | Oleic Acid (18:1) | Linolenic Acid (18:2) | Linoleic Acid (18:3) |
| A1937NMU-85 | 19.8 | 3.6 | 17.4 | 51.3 | 7.7 |
| A1937 Parent | 12.3 | 3.8 | 18.7 | 57.2 | 8.0 |

$M_5$ Progeny from the $M_4$ plant A1937NMU-85 and the A1937 parent were analyzed by gas-liquid chromatography, and the results are set forth in Table II:

TABLE II

| | Fatty Acid Composition | | | | |
|---|---|---|---|---|---|
| Seed Identification | Palmitic Acid (16:0) | Stearic Acid (18:0) | Oleic Acid (18:1) | Linolenic Acid (18:2) | Linoleic Acid (18:3) |
| A1937NMU-85 | 20.1 | 3.8 | 18.5 | 49.9 | 7.6 |
| A1937 Parent | 12.1 | 4.6 | 27.1 | 50.1 | 6.1 |

Seeds of the soybean A1937NMU-85 have been deposited under the terms of the Budapest Treaty at the American Type Culture Collection (ATCC) at 12301 Parklawn Drive, Rockville, Md. 20852, U.S.A. More specifically 2,500 seeds of A1937NMU-85 were deposited on Jun. 18, 1996 and have been assigned ATCC Accession No. 97618.

EXAMPLE 2

This Example describes the preparation of the mutant line ElginEMS-421.

Mutant line ElginEMS-421 was obtained from ethyl methane sulfonate (EMS) treatment of the parent variety Elgin. In May, 1984, 2,500 seeds of Elgin were soaked in 2.5 L distilled water in a 6 L flask for 9 hours at room temperature. The flask was aerated for the 9 hours of soaking. The water was drained from the flask, and 2.5 L of 0.025 molar EMS in 0.1M phosphate buffer at pH 7 were added. The seeds were soaked for 9 hours, the solution was drained and the seeds were rinsed twice with distilled water. Treated seeds were placed in containers to prevent drying and transported to the Agricultural Engineering and Agronomy Research Center near Ames, Iowa. The seeds were planted 2.5 cm deep in moist soil within 4 hours after the last rinse. The soil was watered regularly to keep it moist until seedling emergence. The properties of the mutant seed and their progeny were evaluated beginning with the $M_2$ generation.

A similar number of seeds was harvested from each of the $M_1$ (first mutant generation) plants in a population to obtain 2,000 $M_2$ seeds for each population. A random sample of 1,000 of the second generation $M_2$ seeds from the population was planted in February at the Iowa State University-University of Puerto Rico Soybean nursery at Isabela, Puerto Rico. Five hundred $M_2$ plants were harvested individually from the population, and a 10-seed sample from selected plants was analyzed by gas-liquid chromatography to determine the fatty acid composition. $M_3$ progeny of the mutant plant were planted in Puerto Rico in November, 1986, and the results confirmed the unique fatty acid composition of the $M_2$ parent plant.

Table III sets forth the analysis of the 10-seed sample of the $M_2$ plant from which ElginEMS-421 originated as well as that of its parent:

TABLE III

| | Fatty Acid Composition | | | | |
|---|---|---|---|---|---|
| Seed Identification | Palmitic Acid (16:0) | Stearic Acid (18:0) | Oleic Acid (18:1) | Linolenic Acid (18:2) | Linoleic Acid (18:3) |
| ElginEMS-421 | 17.9 | 3.9 | 18.6 | 50.8 | 8.9 |
| Elgin Parent | 12.1 | 4.4 | 18.7 | 56.0 | 8.8 |

Table IV sets forth the analysis of $M_3$ progeny from the $M_2$ plant ElginEMS-421 and that of its parent:

TABLE IV

| Seed Identification | Fatty Acid Composition | | | | |
|---|---|---|---|---|---|
| | Palmitic Acid (16:0) | Stearic Acid (18:0) | Oleic Acid (18:1) | Linolenic Acid (18:2) | Linoleic Acid (18:3) |
| ElginEMS-421 | 16.9 | 4.1 | 16.8 | 50.2 | 11.9 |
| Elgin Parent | 11.6 | 4.2 | 17.8 | 55.5 | 10.9 |

Seeds of the soybean Elgin EMS-421 have been deposited under the terms of the Budapest Treaty at the American Type Culture Collection (ATCC) at 12301 Parklawn Drive, Rockville, Maryland 20852, U.S.A. More specifically 2,500 seeds of Elgin EMS-421 were deposited on Jun. 18, 1996 and have been assigned ATCC Accession No. 97617.

EXAMPLE 3

This Example describes the crossing of A1937NMU-85 and ElginEMS-421 to obtain the soybean lines of the present invention characterized by high palmitic acid contents.

Crosses were made between individual plants of A1937NMU-85 and ElginEMS-421 at the Agricultural Engineering and Agronomy Research Center near Ames, Iowa, in the summer of 1987. The hybrid $F_1$ seeds obtained from the different plant-to-plant crosses were kept separate, and were designated AX4659 through AX4663 and AX4676.

The $F_1$ seed was planted in the Iowa State University-University of Puerto Rico nursery at Isabela, Puerto Rico, in October, 1987. $F_2$ seeds were obtained by natural self-pollination. Each $F_1$ plant was harvested individually, and the $F_2$ seeds of each were maintained as a separate subpopulation.

Forty $F_2$ seeds from each of the six crosses were planted in Puerto Rico in February, 1988. $F_3$ seeds were obtained by natural self-pollination. $F_2$ plants were harvested individually. A 5-seed sample from each $F_2$ plant was analyzed for fatty acid composition by gas chromatography.

Table V summarizes the analysis of the fatty acid composition of the $F_3$ seeds from individual $F_2$ plants:

TABLE V

| Seed Identification | Fatty Acid Composition | | | | |
|---|---|---|---|---|---|
| | Palmitic Acid (16:0) | Stearic Acid (18:0) | Oleic Acid (18:1) | Linolenic Acid (18:2) | Linoleic Acid (18:3) |
| AX4659-2-3 | 21.3 | 4.1 | 15.9 | 50.4 | 8.2 |
| AX4659-3-7 | 25.9 | 3.7 | 14.2 | 47.9 | 8.3 |
| AX4659-3-8 | 23.9 | 3.7 | 17.5 | 46.6 | 8.2 |
| AX4660-3-4 | 26.1 | 4.5 | 16.2 | 44.9 | 8.3 |
| AX4663-5-2 | 25.9 | 4.4 | 17.7 | 44.4 | 7.5 |
| AX4663-5-4 | 26.8 | 4.1 | 12.5 | 48.2 | 8.3 |
| AX4676-2-11 | 23.6 | 3.6 | 15.7 | 48.7 | 8.4 |
| A1937NMU-85 | 19.0 | 3.8 | 15.7 | 53.2 | 8.2 |
| ElginEMS-421 | 17.4 | 4.0 | 14.6 | 53.0 | 10.9 |

Twelve $F_3$ seeds from each selected $F_2$ plant were planted in the Iowa State University-University of Puerto Rico nursery in October 1988. $F_4$ seeds were obtained natural self-pollination. Each $F_3$ plant was harvested individually. A 10-seed sample from each $F_3$ plant was analyzed for fatty acid composition by gas chromatography.

Table VI summarizes the analysis of the fatty acid composition of the $F_4$ seeds from individual $F_3$ plants:

TABLE VI

| Seed Identification | Fatty Acid Composition | | | | |
|---|---|---|---|---|---|
| | Palmitic Acid (16:0) | Stearic Acid (18:0) | Oleic Acid (18:1) | Linolenic Acid (18:2) | Linoleic Acid (18:3) |
| AX4659-2-3-9 | 27.8 | 3.8 | 13.9 | 44.1 | 10.3 |
| AX4659-3-7-7 | 27.4 | 3.5 | 15.1 | 44.4 | 9.6 |
| AX4659-3-8-6 | 27.4 | 3.4 | 16.1 | 42.8 | 10.3 |
| AX4660-3-4-4 | 27.7 | 3.8 | 15.6 | 43.2 | 9.7 |
| AX4663-5-2-9 | 28.0 | 3.9 | 13.1 | 43.0 | 12.0 |
| AX4663-5-4-5 | 28.3 | 4.0 | 12.4 | 43.8 | 11.5 |
| AX4676-2-11-8 | 28.2 | 3.7 | 12.1 | 44.3 | 11.7 |
| A1937NMU-85 | 19.6 | 3.9 | 17.5 | 50.1 | 8.9 |
| ElginEMS-421 | 16.6 | 4.0 | 19.8 | 49.0 | 10.6 |

Thirty $F_4$ seeds from each selected $F_3$ plant were planted at the Agricultural Engineering and Agronomy Research Center near Ames, Iowa, in May, 1989. $F_5$ seeds were obtained by natural self-pollination. Each $F_4$ plant was harvested individually. A 5-seed sample from each of 10 $F_4$ plants tracing to an $F_3$ plant were analyzed for fatty acid composition by gas chromatography.

Table VII summarizes the analysis of the fatty acid composition of the $F_5$ seeds from individual $F_4$ plants, the parents, and C1727:

TABLE VII

| Seed Identification | Fatty Acid Composition | | | | |
|---|---|---|---|---|---|
| | Palmitic Acid (16:0) | Stearic Acid (18:0) | Oleic Acid (18:1) | Linolenic Acid (18:2) | Linoleic Acid (18:3) |
| AX4659-2-3-9 | 25.7 | 3.8 | 14.6 | 46.2 | 9.6 |
| AX4659-3-7-7 | 26.1 | 3.9 | 14.0 | 45.2 | 10.7 |
| AX4659-3-8-6 | 25.0 | 4.5 | 20.4 | 42.1 | 7.9 |
| AX4660-3-4-4 | 26.6 | 4.0 | 15.1 | 44.6 | 9.6 |
| AX4663-5-2-9 | 26.4 | 4.1 | 15.7 | 43.0 | 10.7 |
| AX4663-5-4-5 | 25.6 | 4.2 | 16.6 | 44.0 | 9.6 |
| AX4676-2-11-8 | 25.2 | 4.0 | 17.4 | 44.3 | 9.1 |
| A1937NMU-85 | 18.8 | 5.0 | 20.7 | 48.3 | 7.2 |
| ElginEMS-421 | 15.7 | 4.1 | 19.7 | 50.7 | 9.8 |
| C1727 | 15.6 | 3.6 | 19.2 | 53.2 | 8.4 |

EXAMPLE 4

This Example describes the crossing of AX4663-5-4-5 with A89-259098, a high stearic acid line, to obtain a soybean line according to the present invention characterized by an exceptionally high palmitic acid content.

2,500 seeds of AX4663-5-4-5 were deposited on Dec. 26, 1995 at the American Type Culture Collection (ATCC) at 12301 Parklawn Drive, Rockville, Md. 20852, U.S.A. and have been assigned ATCC Accession No. 97393.

1,250 seeds of A89-259098 were deposited on Dec. 26, 1995 at the American Type Culture Collection (ATCC) at 12301 Parklawn Drive, Rockville, Md. 20852, U.S.A., and have been assigned ATCC Accession No. 97391. An additional 1,250 seeds of A89-259098 were deposited on Apr. 22, 1996.

Parent line AX4663-5-4-5 was obtained as described in Example 3. Parent line A89-259098 was obtained as described in our copending application, Ser. No. 07/643,277. The hybrid $F_1$ seeds obtained from the cross were designated AX7016-AX7019.

$F_1$ seeds of the cross were planted in February, 1990, in the Iowa State University-University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations.

Four individual $F_2$ seeds from each $F_1$ plant were split so that the embryonic axis was left intact. The portion without the embryonic axis (approximately one-third of the seed) was analyzed for fatty acid composition by gas chromatography.

Table VIII summarizes the analysis of the fatty acid composition of an $F_2$ seed having the desired high palmitic acid content and that of the parent lines:

TABLE VIII

| | Fatty Acid Composition | | | | |
|---|---|---|---|---|---|
| Seed Identification | Palmitic Acid (16:0) | Stearic Acid (18:0) | Oleic Acid (18:1) | Linolenic Acid (18:2) | Linoleic Acid (18:3) |
| AX7017-1-3 | 30.4 | 5.2 | 10.1 | 42.6 | 11.7 |
| AX4663-5-4-5 | 28.6 | 4.0 | 11.9 | 43.0 | 12.4 |
| A89-259098 | 8.0 | 30.3 | 21.5 | 34.6 | 5.6 |

What is claimed is:

1. A soybean seed designated ElginEMS-421 having ATCC Accession No. 97617 and its descendents which are capable of yielding an endogenously formed vegetable oil exhibiting a palmitic acid content of at least 15.7% by weight based upon the total fatty acid content.

2. A soybean seed according to claim 1 wherein the vegetable oil endogenously formed therein contains palmitic acid in a concentration of approximately 16.9 percent by weight, stearic acid in a concentration of approximately 4.1 percent by weight, oleic acid in a concentration of approximately 16.8 percent by weight, linoleic acid in a concentration of approximately 50.2 percent by weight, and linolenic acid in a concentration of approximately 11.9 percent by weight as determined by gas chromatography.

3. Soybean seeds according to claim 1 hat are provided as an assemblage of such seeds.

4. A soybean plant produced by the seed of claim 1.

* * * * *